United States Patent [19]

Flynn et al.

[11] 4,146,037

[45] Mar. 27, 1979

[54] CARDIAC PACER ELECTRODE AND LEAD INSERTION TOOL

[75] Inventors: Jerome R. Flynn, St. Paul; Tom G. Victor, Minneapolis; David E. Reimer, Osseo; David J. Parins, St. Paul, all of Minn.

[73] Assignee: Cardiac Pacemakers, Inc., St. Paul, Minn.

[21] Appl. No.: 859,323

[22] Filed: Dec. 12, 1977

[51] Int. Cl.$^2$ .............................................. A61N 1/04
[52] U.S. Cl. ................................................. 128/419 P
[58] Field of Search ................... 128/404, 418, 419 P, 128/2.06 E, DIG. 4

[56] References Cited

U.S. PATENT DOCUMENTS

| 3,533,403 | 10/1970 | Woodson | 128/419 P |
| 3,750,650 | 8/1973 | Ruttgers | 128/418 |
| 3,875,947 | 4/1975 | Jula | 128/418 |

*Primary Examiner*—William E. Kamm
*Attorney, Agent, or Firm*—Orrin M. Haugen; Thomas J. Nikolai

[57] ABSTRACT

A guide tube means for assisting in the fixation of an electrode to the heart of a patient, with the guide tube means being adapted for releasable retention of the electrode and its associated leads, the guide tube means including a lead-retaining sleeve along with a rod means for controllably dislodging the leads from the sleeve. The rod means includes means for releasably retaining the insulative backing or pad for the electrode, and is further provided with a radially extending ear for dislodging the electrode lead from the sleeve upon withdrawal of the rod means from the sleeve, thereby providing for the formation of a slack loop or segment adjacent the site of the electrode, the slack portion permitting relative motion to occur between the end of the guide tube and the electrode as fixed in position.

3 Claims, 6 Drawing Figures

CARDIAC PACER ELECTRODE AND LEAD INSERTION TOOL

BACKGROUND OF THE INVENTION

The present invention relates generally to an improved guide tube arrangement for assisting in the handling of a cardiac pacer electrode and lead assembly during fixation of the electrode to the heart of a patient, and more specifically to such a guide tube means which employs a coaxially arranged rod which releasably retains the electrode and its insulative pad and which is arranged to dislodge the electrode lead from the sleeve or tube upon withdrawal of the rod from the sleeve.

A significant feature of the guide tube means of the present invention is the formation of a slack segment or loop adjacent the site of the fixed electrode substantially immediately upon release of the electrode and its insulative pad from the guide tube assembly.

Devices for assisting in the fixation or securing of electrodes into body tissue have been known in the past and utilized. Certain of these devices are disclosed in U.S. Pat. No. 3,875,947. In these devices, however, the arrangement is such that the electrode remains secured to the guide tube means until full release of the lead has been achieved. Also, no slack segment or loop is provided until the electrode and lead assembly are substantially fully released from the guide device.

Electrodes having a helical shape are in common usage at this time. Such devices are disclosed in U.S. Pat. No. 4,011,861, among others. Such electrodes have the advantage of being sutureless upon fixation. Furthermore, fixation is reasonably stable, and dislodgement has not been an ordinary or frequent complication. In order to avoid entanglement or application of torque to the lead member, particularly in the area adjacent the point where the insulative pad joins the cylindrical lead, means such as a slotted tube have been proposed for avoiding the generation of such forces.

As will be appreciated, a helical electrode will ordinarily be provided in an assembly which includes the electrode structure per se, the conductive leads which are arranged to couple the electrode to the pulse generator, and an insulative backing or pad member which isolates and insulates the junction point between the conductors of the leads and the electrode. The insulative backing or pad further provides a means for delivering torque to the helical electrode for fixation.

The electrode leads are normally insulated with silicone rubber, with such material being inert to body fluids, and further providing a high degree of flexibility for the assemblies. Examples of such conductive leads are found in U.S. Pat. No. 4,033,355, among others. Because of the flexibility of the leads, precautions should be taken in order to avoid having the leads becoming entangled during the implant operation, and specifically during fixation. Apparatus of the type including a slotted guide tube has been helpful in confining the leads during the fixation operation.

SUMMARY OF THE INVENTION

Generally, and in accordance with the present invention, a guide tube means is provided for assisting in the handling of the lead during the implant operation, with the guide tube means including a slotted sleeve member having a rod means disposed generally coaxially therewithin. The slotted portion of the sleeve provides an elongated anchoring point for the lead members, and the rod means provides a releasable retainer for the insulative backing pad adjacent the electrode, and further provides a means for dislodging the lead from the slot in the sleeve upon withdrawal of the rod means from the sleeve. Ordinarily, the rod means has a length which exceeds the length of the sleeve so that a portion of the length of the rod extends outwardly to form a gripping member. As has been indicated, upon release of the electrode from the guide tube means, there is a substantial slack loop available so that any relative motion that may occur between the guide tube means and the electrode which is fixed in place, will not apply or establish any unusual force unless, of course, excessive relative movement occurs. The slack loop is sufficient, however, to accommodate the inadvertent motion which frequently occurs during this manipulation of the surgeon, in spite of the fact that the surgeon may have extreme manual dexterity. The insulative backing for the electrode is provided with means for releasable attachment to the rod, with the preferred means being a pair of spaced bores being formed in the backing member. This substantially reduces the cross-sectional thickness required for this member, with this reduction in cross-section being desirable for physiological reasons.

Therefore, it is a primary object of the present invention to provide an improved guide tube means which is adapted to assist in the fixation of a cardiac pacer electrode and lead assembly to the heart, and wherein the guide tube means provides for releasable retention of the leads along with the electrode-insulative pad assembly.

It is a further object of the present invention to provide an improved guide tube means for use in a sutureless myocardial electrode, and wherein the guide tube means provides a control for the retention of the electrode and lead, and which provides a significant degree of freedom of movement by the surgeon of the guide tube means upon release of the electrode from the guide tube assembly.

It is yet a further object of the present invention to provide an improved guide tube means for use in the fixation of a sutureless myocardial electrode, and wherein the guide tube means is arranged to provide the surgeon with a slack segment or loop in the leads upon release of the electrode and its associated insulative pad from the guide tube means.

Other and further objects of the present invention will become apparent to those skilled in the art upon a study of the following specification, appended claims, and accompanying drawing.

DESCRIPTION OF THE PREFERRED EMBODIMENT

Figure 1:
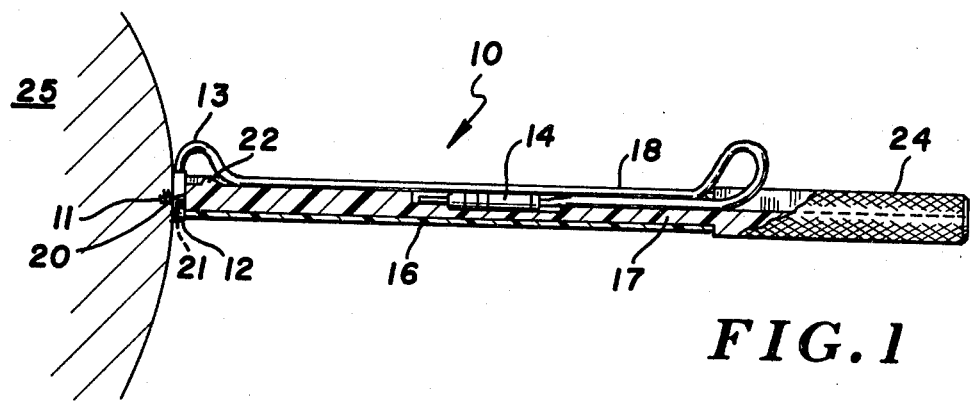
FIG. 1 is a sectional view of the guide tube means of the present invention, and illustrating the assembly following fixation of an electrode to the heart, and further illustrating the disposition of the leads within the guide tube following such fixation.

In accordance with the preferred embodiment of the present invention, and with particular attention being directed to FIG. 1, the guide tube means generally designated 10 for cardiac pacer electrode and lead assemblies is shown in fully assembled form. The electrode is shown at 11, in the form of a helically wound member, with the electrode 11 extending from the insulated backing pad 12. Lead 13 extends outwardly from pad 12, and continues to the coupling terminal 14. As is appreciated, lead 13 is in the form of a wound conductor insulatively coated with a layer of silicone rubber or other substance inert to body fluids. The configuration of the electrodes may be that illustrated in U.S. Pat. No. 4,033,355, as well as that disclosed and claimed in U.S. application Ser. No. 691,032, filed May 28, 1976, entitled "SEALING ARRANGEMENT FOR HEART PACER ELECTRODE LEADS", and assigned to the same assignee as the present invention. The guide tube means 10 includes a sleeve 16 together with a coaxially arranged rod 17, with sleeve 16 having a slot or groove formed therein as at 18. Rod 17 has a distal end as at 20, from which a pair of drive pins 21—21 extend. An electrode dislodging projection 22 is provided for forcing lead 13 outwardly from the confines of slot 18, as will be more fully explained hereinafter. Gripping handle 24 is available for sliding rod 17 outwardly of sleeve 16, as will be more fully explained hereinafter as well. Also, a cavity 17A is formed within rod 17 to receive and retain the terminal of lead 13 without requiring 30 external storage or disposition of this portion of lead 13.

In the embodiment of FIG. 1, electrode 11 is shown fixed within the muscular tissue 25, such as the heart in a cardiac pacer electrode embodiment.

Figure 2:
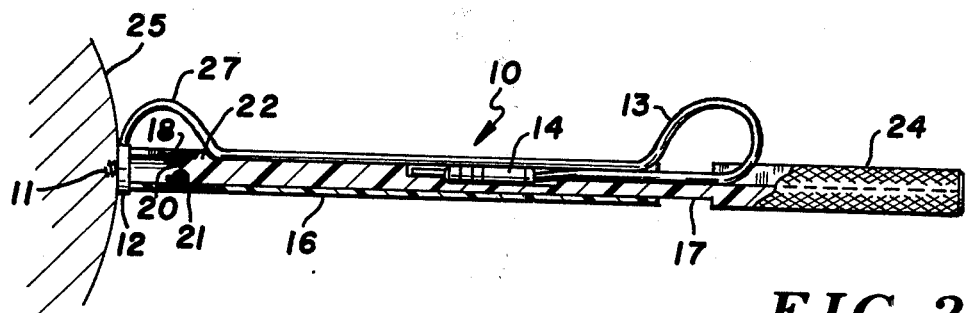
FIG. 2 is a view similar to FIG. 1, and illustrating the arrangement of the guide tube means of the present invention immediately following release of the electrode and its insulative pad from the guide tube means, and further illustrating the formation of the slack segment in the electrode.

Attention is now directed to FIG. 2 of the drawing wherein the guide tube means is illustrated after initial retraction or removal of rod 17 from sleeve 16. As is apparent, drive pins 21—21 are removed or disengaged from pad 12, with pad 12 accordingly being fully released. The loop portion 27 is provided with the electrode, so as to avoid transmission of undesired forces to the electrode which has already been fixed in place.

Figure 3:
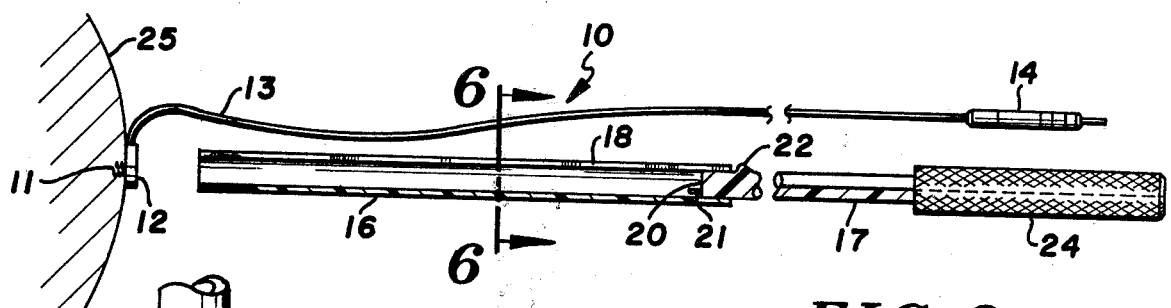
FIG. 3 is a view similar to FIGS. 1 and 2, and illustrating the configuration of the guide tube means following substantially complete removal of the coaxial rod from the sleeve, with FIG. 3 being shown on a slightly reduced scale.

Attention is now directed to FIG. 3 of the drawing wherein the rod 17 is shown substantially fully withdrawn or extended from sleeve 16, and wherein the lead 13 has been fully dislodged from the slot 18. In this disposition, of course, the lead is free and in a configuration proper for attachment to the pulse generator.

Figures 4, 5:
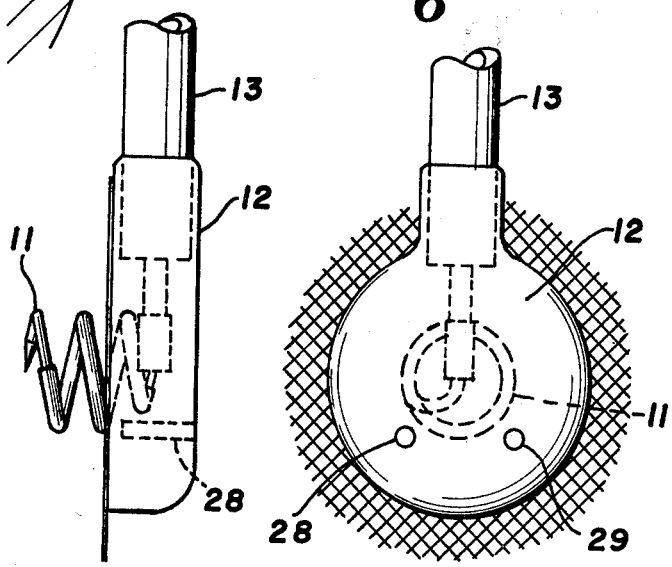
FIG. 4 is a side elevational view of the electrode and its associated insulative pad, and further illustrating a segment only of the lead, with the balance of the lead being broken away.
FIG. 5 is a top plan view of that portion of the electrode assembly illustrated in FIG. 4, and showing the location of the drive pin receiving holes.

Attention is now directed to FIGS. 4 and 5 of the drawing wherein the drive pin receiving holes are illustrated. Drive pin receiving holes are shown as at 28 and 29, with these holes being adapted to receive drive pins 21—21. An interference fit is provided between the outer circumference of drive pins 21—21 and pin receiving holes 28 and 29 so as to provide some retention and engaging of the pad 12 to the pins 21—21. In this arrangement, therefore, rotation of the guide tube means will, in turn, cause corresponding rotation of electrode 11 and pad 12, and thus achieve fixing of the electrode in a sutureless fashion.

Figure 6:
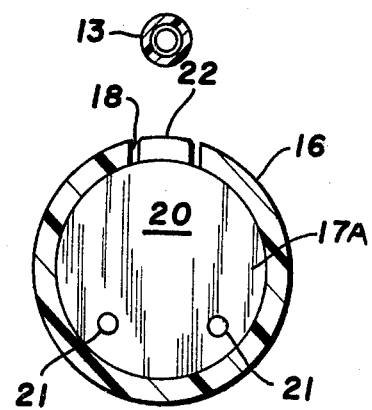
FIG. 6 is a vertical sectional view taken along the line and in the direction of the arrows 6—6 of FIG. 3.

Attention is now directed to FIG. 6 of the drawing wherein the guide tube means is illustrated in section. The telescopingly engaging rod and sleeve are illustrated, together with the projection 22 for dislodging of the electrode lead 13 from slot 18.

In actual operation, therefore, the assembly as illustrated in FIG. 1 is grasped by the surgeon and with electrode 11 in contact with the heart, the entire assembly is rotated about its axis so as to cause the threaded electrode to engage and enter the heart. Rotation is continued until the electrode is properly fixed and seated, whereupon rod 17 is initially withdrawn, as is shown in the configuration of FIG. 2. Initial withdrawal of rod 17 from sleeve 16 causes pins 21—21 to become disengaged from pin receiving holes 28 and 29, thereby freeing the electrode and the insulative pad from the remaining components of the system. Also, the initial retraction or removal of rod 17 from sleeve 16 causes the loop 27 to become enlarged, thereby providing an additional degree of freedom of motion for the surgeon's hands. Continued withdrawal of rod 17 from sleeve 16 is undertaken until the arrangement assumes the configuration of FIG. 3, with the lead thereupon being fully withdrawn or removed from the slot 18.

As has been indicated, the materials of construction for the electrode and the leads are conventional, and those materials conventionally utilized are adapted to this system. The sleeve 16 may be formed of any suitable rigid plastic material, such as methyl methacrylate or the like. Rod 17 is preferably formed of a material which has a low coefficient of friction, with one such material being polytetrafluoroethylene. Molded polytetrafluoroethylene is commercially available. Of course, other materials may be utilized if desired, either plastics or metals being adapted for the system.

We claim:

1. In combination with a cardiac pacer electrode and lead assembly; guide tube means for manipulation of said electrode and said electrode lead assembly for fixation of said electrode to the heart of a patient, wherein said electrode includes pad means for retaining said electrode therewithin; said guide tube means comprising:
    (a) sleeve means having an axial slot formed therein and extending along the length thereof and arranged for the retention of the electrode lead assembly therewithin;
    (b) rod means disposed coaxially within said sleeve means and having a radially extending projection formed adjacent the distal end thereof for dislodging said electrode lead assembly from the slot of said sleeve, means secured to the distal end of said rod means for releasably engaging said pad means, said rod means having a length exceeding the length of said sleeve means and wherein a portion of the length of said rod means extends outwardly from the proximal end of said guide tube means for engagement with said pad means; and
    (c) the arrangement being such that upon withdrawal of said rod means from said sleeve means the pad of said electrode lead assembly is released from said rod means and wherein further withdrawal of said rod means dislodges the electrode lead from the slot formed within said sleeve means.

2. The cardiac pacer electrode and lead assembly as defined in claim 1 being particularly characterized in that the means on said rod means for releasably engaging said pad means consists of a pair of axially extending drive pins arranged to mate with bores formed in the outer surface of said pad means.

3. The cardiac pacer electrode and lead assembly as defined in claim 1 being particularly characterized in that the projection formed on said rod means extends generally radially outwardly to an amount substantially equal to the wall thickness of said sleeve means.

* * * * *